July 13, 1943. C. MALLERIN Plant Pat. 596
ROSE PLANT
Filed Jan. 19, 1943
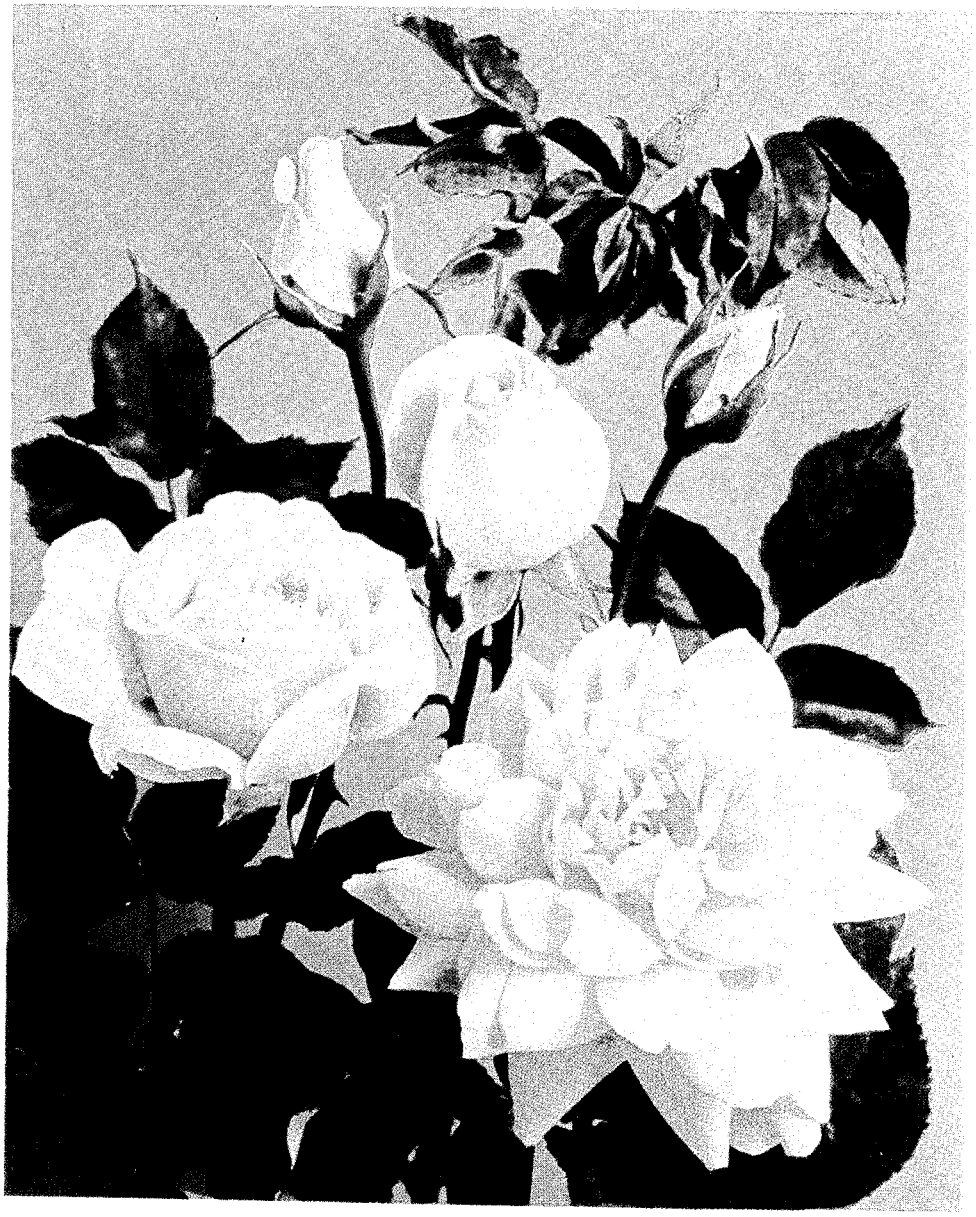
Inventor
Charles Mallerin
By Robert Robb
Attorney.

Patented July 13, 1943

UNITED STATES PATENT OFFICE

596

ROSE PLANT

Charles Mallerin, Varces, par Pont de Claix, France, assignor to The Conard-Pyle Company, West Grove, Pa.

Application January 19, 1943, Serial No. 472,892

1 Claim. (Cl. 47—61)

The present invention relates to a new and distinct variety of rose plant of the hybrid tea class, resulting from a cross of the "Julien Potin" and "Gitane" varieties.

The seed parent of this new variety has long been noted as one of the world's best clear yellow roses and its influence upon this union of two fine roses is clearly shown in the present variety which for its combination of form, color of flowers, and excellence of growth represents a decided improvement in the hybrid tea class.

The distinctive characteristics of this new rose are set forth more specifically in the following detail description in which color terminology accords with Ridgway's Color Standard:

Type: Hardy; tall; bush; outdoor; seedling; for garden decoration.
Class: Hybrid tea.
Parentage:
*Seed parent.*—Julien Potin.
*Pollen parent.*—Gitane.
Propagation: Holds its distinguishing characteristics through succeeding propagations by budding, which is the only method employed up to the present time.

*Flower*

Locality where grown: West Grove, Pennsylvania.
Flowers borne: Singly and several to stem; on normal, medium length stems.
Quantity of bloom: Free, outdoors.
Continuity: Intermittent.
Fragrance: Slight; spicy.
Bud:
*Peduncle.*—Medium length; heavy; erect; Oil-Green, Plate V; entirely smooth.
*Before calyx breaks.*—*Size*—medium. *Form*—ovid with an inconspicuous neck, with foliaceous appendages on the surface of the bud, with slender bristle like foliaceous parts extending beyond the tip of the bud equal to ¼ or more of its length.
*As calyx breaks.*—*Color*—Light Cadmium, Plate IX, tinted Carmine, Plate I.
*As first petal opens.*—*Size*—medium. *Form*—globular. *Color*—outside—Lemon-Chrome base, Plate IV, to Light Cadmium at tip, Plate IV; inside—Lemon-Chrome base, Plate IV, to Light Orange Yellow at tip, Plate III. *Opening*—opens up well.
Bloom:
*Size.*—When fully open—large, 4¼ to 4½ inches.
*Petalage.*—Very double; from forty to forty-five arranged irregularly.
*Form.*—Cupped, high center at first; becoming flat; petals remaining at first very loosely rolled outward; becoming later, at maturity, rolled outward.
Petals: Leathery, with inside satiny and outside satiny.
*Shape.*—*Outside*—obovate, scalloped with apex flat, with 2 notches. Intermediate—obovate, with 1 notch. Inside—obovate with apex with 1 notch.

This description of a newly opened flower was made from a rose grown outdoors, in the month of August, 1941, at West Grove, Pennsylvania.

*Color.*—Outside petal: outside surface—Light Cadmium, Plate IV; inside surface—Light Cadmium to Apricot Yellow, Plate IV. Intermediate petal—outside surface—Apricot Yellow to Buff-Yellow, Plate IV; inside surface—Apricot Yellow to Buff-Yellow, Plate IV. Inner petal—outside surface—Apricot Yellow to Buff-Yellow, Plate IV; inside surface—Apricot Yellow to Buff-Yellow, Plate IV.

This description was made from a rose that was open for three days, outdoors, in the month of August, 1941, at West Grove, Pennsylvania.

*Color.*—Outside petal: outside surface—Buff-Yellow, Plate IV; inside surface—Maise-Yellow, Plate IV. Inside petal: outside surface—Buff-Yellow, Plate IV; inside surface—Maize-Yellow, Plate IV.
*General color effect.*—Newly opened flower—Mikado orange center, Plate III; outside petals, Light Orange Yellow, Plate III. Three days open—Orange-Buff center; outside petals, Pale Orange Yellow, Plate III.
*Behavior.*—Drop off cleanly; fading Maize-Yellow, Plate IV.
*Flower longevity.*—On bush in garden, four to five days in August. Cut roses grown outdoors kept at living room temperatures, three to five days in August.

*Reproductive organs*

Stamens: Medium number arranged irregularly partly about pistils.
Filaments: Medium length; Brazil Red, Plate I, many without anthers.
Anthers: Medium size; Antique-Brown, Plate III, open at various times.
Pollen: Moderate; Buff-Yellow, Plate IV.
Pistils: Medium number.
Styles: Uneven; medium length; thin; loosely bunched.
Stigma: Capucine-Orange, Plate III.
Ovaries: All enclosed in calyx.
Hips: None.

Sepals: Permanent; moderately long, spear-shaped, recurved.
Seeds: None.

*Plant*

Foliage:

*Leaves.*—Compound of 3, 5 leaflets; normal amount; medium size; leathery, glossy, wrinkled.

*Leaflets.*—Ovoid with apex mucronate; base obtuse; margin simply serrate.

*Color.*—*Mature:* upper surface—Dark Yellow-Green, Plate XXXII; under surface—Rainette-Green, Plate XXXI. *Young:* upper surface—Rainette-Green, Plate XXXI, edged Hays Russet, Plate XIV; under surface—Rainette-Green, Plate XXXI, suffused Hays Russet, Plate XIV.

*Rachis* (the supporting stem of the compound leaf).—Medium weight. Upper side—smooth, grooved; under side—smooth, with a few thorns.

*Stipules.*—Medium length; moderately wide; with medium points, turning out at an angle of less than 90°, recurved toward the stem.

*Disease.*—Resistant to mildew, blackspot.

Growth:

*Habit.*—Bushy; branched.

*Growth.*—Vigorous.

*Canes.*—Moderately heavy.

*Main stems.*—Bright Cress-Green, Plate XXXI. *Thorns*—several; short; hooked downward; with broad base. *Prickles*—few; Morocco Red, Plate I. *Hairs*—none.

*Branches.*—Dull Jade-Green, Plate XXXI. *Thorns*—several; short; straight and also hooked downward; with narrow base. *Prickles*—none. *Hairs*—none.

*New shoots.*—Bright Rainette-Green, Plate XXXI. *Thorns*—several; medium length; hooked downward; with narrow base. *Prickles*—none. *Hairs*—none.

I claim:

A new and distinct variety of hybrid tea rose plant characterized as to novelty by its habits of growth and form, and the novel color combination of its blooms in their various stages of development, substantially as shown and described.

CHARLES MALLERIN.